(12) United States Patent
Yang et al.

(10) Patent No.: US 8,883,670 B2
(45) Date of Patent: Nov. 11, 2014

(54) MO CONTAINING CATALYST, A PREPARATION METHOD AND A METHOD FOR PREPARING METHYL MERCAPTAN

(75) Inventors: Yiquan Yang, Xiamen (CN); Aiping Chen, Xiamen (CN); Qi Wang, Xiamen (CN); Jan-Olaf Barth, Frankfurt (DE); Christoph Weckbecker, Gründau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 1646 days.

(21) Appl. No.: 12/439,926

(22) PCT Filed: May 25, 2007

(86) PCT No.: PCT/EP2007/055078
§ 371 (c)(1),
(2), (4) Date: Nov. 13, 2009

(87) PCT Pub. No.: WO2008/031637
PCT Pub. Date: Mar. 20, 2008

(65) Prior Publication Data
US 2010/0094059 A1  Apr. 15, 2010

(30) Foreign Application Priority Data

Sep. 11, 2006 (CN) .......................... 2006 1 0151777

(51) Int. Cl.
| | | |
|---|---|---|
| *B01J 27/057* | (2006.01) |
| *B01J 21/04* | (2006.01) |
| *B01J 21/08* | (2006.01) |
| *B01J 39/14* | (2006.01) |
| *B01J 23/28* | (2006.01) |
| *B01J 37/02* | (2006.01) |
| *B01J 23/887* | (2006.01) |
| *C07C 319/02* | (2006.01) |
| *B01J 35/00* | (2006.01) |
| *B01J 37/20* | (2006.01) |

(52) U.S. Cl.
CPC .............. *B01J 23/28* (2013.01); *B01J 37/0201* (2013.01); *B01J 37/0205* (2013.01); *B01J 35/002* (2013.01); *B01J 23/8872* (2013.01); *B01J 21/08* (2013.01); *B01J 37/20* (2013.01); *C07C 319/02* (2013.01); *B01J 37/0203* (2013.01); *B01J 27/0576* (2013.01)
USPC ........................... 502/120; 502/215; 502/321

(58) Field of Classification Search
None
See application file for complete search history.

(56) References Cited

U.S. PATENT DOCUMENTS 3,939,208 A * 2/1976 Cavaterra et al. .............. 568/479
4,049,575 A * 9/1977 Sasaki et al. ................... 502/202
(Continued)

FOREIGN PATENT DOCUMENTS

| CN | 1207958 A | 2/1999 |
|---|---|---|
| CN | 1998118187 | 2/1999 |

(Continued)

OTHER PUBLICATIONS

Bart, J. C. J. et al. Journal of Materials Science, 1975, 10, 1029-1036.*

(Continued)

*Primary Examiner* — Jafar Parsa
*Assistant Examiner* — Medhanit Bahta
(74) *Attorney, Agent, or Firm* — Smith, Gambrell & Russell, LLP

(57) ABSTRACT

A method is described to prepare a Mo containing supported catalyst comprising $TeO_2$ as active promoter and a process for preparing methanethiol in the presence of said catalyst.

6 Claims, 1 Drawing Sheet

X-ray diffractograms of the catalyst $TeO_3$-$K_2MoO_4/SiO_2$ and comparing samples

(56) References Cited

U.S. PATENT DOCUMENTS

| | | | |
|---|---|---|---|
| 4,665,245 A | 5/1987 | Quann | |
| 5,283,369 A | 2/1994 | Clark et al. | |
| 5,493,058 A | 2/1996 | Cadot | |
| 6,084,135 A * | 7/2000 | Wachs | 568/482 |
| 6,645,905 B2 * | 11/2003 | Gaffney et al. | 502/311 |
| 2005/0176989 A1 * | 8/2005 | Coleman et al. | 562/11 |
| 2005/0209469 A1 * | 9/2005 | Shutt et al. | 549/523 |
| 2007/0213564 A1 * | 9/2007 | Yang et al. | 568/70 |

FOREIGN PATENT DOCUMENTS

| | | |
|---|---|---|
| CN | 19981018186 | 2/1999 |
| EP | 104507 A1 | 4/1984 |
| EP | 167354 | 1/1986 |
| EP | 0649837 A1 | 10/1994 |
| FR | 9312491 | 10/1993 |
| GB | 2362382 A | 11/2001 |
| WO | 2005/040082 A2 | 5/2005 |
| WO | WO 2005040082 A2 * | 5/2005 |

OTHER PUBLICATIONS

International Search Report.

Y-Q Yang et al., "Study of the Supported KsMo04 Catalyst for Methanethiol Synthesis . . . ", Catalysis Letters, Springer, Dordrecht, NL, vol. 74, No. 3-4, 2001; pp. 221-225.

International Preliminary Reort on Patentability.

* cited by examiner

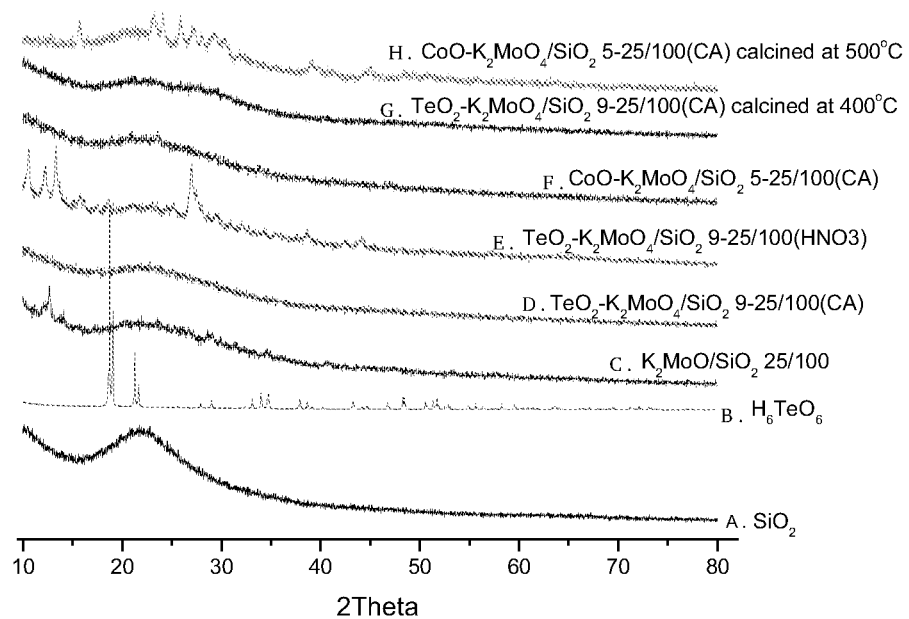
X-ray diffractograms of the catalyst $TeO_2$-$K_2MoO_4/SiO_2$ and comparing samples

MO CONTAINING CATALYST, A PREPARATION METHOD AND A METHOD FOR PREPARING METHYL MERCAPTAN

INTRODUCTION AND BACKGROUND

The invention relates to a process for the preparation of a Mo and Te containing catalyst, and the catalyst itself, useful for methanethiol synthesis from syngas preferably containing high amounts of $H_2S$.

THE PRIOR ART

As an important chemical educt for the production of methionine, pesticides and medicine, methanethiol is predominantly prepared by the reaction of hydrogen sulfide with methanol. For example, U.S. application Ser. No. 856,232 discloses a methanethiol synthesis method based on the reaction of hydrogen sulfide with methyl alcohol or diethyl ether; FR appl. 93,112,491 discloses a preparation method based on the reaction of methyl thio-ether with hydrogen over a transition metal catalyst; EP167,354 discloses a synthesis pathway with a catalyst based on titanium dioxide support and containing NiO or $MoO_3$ as active components for the reaction of hydrogen sulfide with carbon monoxide; Chinese patent applications CN1207957 and CN98118187.2 disclose two catalysts for methyl mercaptan synthesis from syngas containing high amounts of $H_2S$, in which the active component Mo—S—K is formed from the precursor of $K_2MoS_4$ or $(NH_4)_2MoS_4$ plus one potassium salt; WO 2005/040082 discloses two Mo—O—K/$SiO_2$ catalysts for the methanethiol synthesis, wherein the promoters are chosen from the group consisting of oxides of Co, Ni, Fe, Mn or La and Ce, whereby the active component Mo—O—K is formed from $K_2MoO_4$ or $(NH_4)_6Mo_7O_{24}\cdot4H_2O$ plus a potassium salt as precursors.

STATEMENT OF THE INVENTION

The object of this invention is the preparation of catalysts with high activity and selectivity for the one-step methanethiol synthesis from syngas, preferably containing high amounts of $H_2S$. This means preferably a content in the range of 50 to 80 Vol. % $H_2S$.

BRIEF DESCRIPTION OF DRAWING

The Invention will be further understood with reference to the drawing which shows x-ray diffractogram of the catalyst $TeO_2$—$K_2MoO_4$/$SiO_2$ compared with other catalysts.

DETAILED DESCRIPTION OF THE INVENTION

The catalyst according to the invention comprises active components, active promoters and a support material. It is directed to a supported catalyst comprising
  a) a Mo containing and a K containing compound as active components, whereby Mo and K can be constituents of the same compound,
  b) a promoter, wherein the promoter comprises $TeO_2$ and
  c) an oxidic carrier.

Said active component is preferably a Mo—O—K-based active center. Precursors of the Mo and K containing compounds are
  a) $K_2MoO_4$ or
  b) $(NH_4)_6Mo_7O_{24}\cdot4H_2O$ denoted by $MoO_3$ plus a potassium salt denoted as a $K_2O$ precursor or
  c) $MoO_3$ plus one kind of potassium salt, said potassium compound is at least one chosen from the group comprising $K_2CO_3$, KOH and $CH_3COOK$ or any other potassium containing compound being known as a $K_2O$ precursor.

Said promoter is a Te-containing compound denoted by $TeO_2$ whereby $H_6TeO_6$ ($H_2TeO_4\times2\ H_2O$) or any other Te-containing salts or compounds being suitable as $TeO_2$-precursors are used, also a potassium salt of said telluric acid $H_6TeO_6$.

Said support is preferably $SiO_2$ or an oxidic carrier such as $TiO_2$, $ZrO_2$, $Al_2O_3$, $Al_2O_3$—$SiO_2$, zeolites, pure or mixtures of said metal oxides.

For the catalyst $TeO_2$—$K_2MoO_4$/$SiO_2$ (prepared from $K_2MoO_4$) the weight ratio is $TeO_2/K_2MoO_4/SiO_2$=(1-20)/(1-50)/100, more preferably (3-12)/(15-30)/100, for the catalyst $TeO_2$—$MoO_3$—$K_2O$/$SiO_2$ (prepared for example from $(NH_4)_6Mo_7O_{24}\cdot4H_2O$ and a potassium containing salt) the weight ratio is $TeO_2/MoO_3/K_2O/SiO_2$=(1-20)/(1-50)/(1-50)/100, more preferably (3-12)/(15-30)/(8-20)/100.

The invention is also directed to a method to prepare a catalyst according to claim 1, comprising the steps:
  a) impregnating said carrier in more than one step with one or more aqueous solutions comprising a Te containing compound which acts as a $TeO_2$ precursor and a K containing compound which acts as a $K_2O$ precursor and $(NH_4)_6Mo_7O_{24}$ or $MoO_3$ as Mo containing compounds; or
  b) impregnating said carrier in more than one step with one or more aqueous solutions comprising a Te containing compound which acts as a $TeO_2$ precursor and $K_2MoO_4$;
  c) drying the received impregnated carrier; and
  d) optionally treating said impregnated carrier with $H_2$ or syngas (CO+$H_2$) or a syngas and $H_2S$ at elevated temperatures, preferably 200 to 450° C.

Products which are not pre-treated with said gases are also part of the invention.

The formulas of catalysts prepared are expressed as $TeO_2/K_2MoO_4$/carrier or $Teo_2/MoO_3/K_2O$/carrier.

Being exposed to a hydrogen sulphide containing atmosphere the oxidic compounds of Mo, K, Te comprised in the catalyst are converted into sulphides in complete or partially. That means that oxides or sulfides or mixtures of both are contained on the catalyst carrier.

XPS-spectra of said sulfided catalysts modified by different amounts of $TeO_2$ show, that there are higher relative concentrations of $Mo^{4+}$ and $Mo^{5+}$ on the surface of the TeO2-promoted catalysts as compared to $K_2MoO_4$/carrier (especially $SiO_2$), accompanied by lower concentrations of $Mo^{6+}$ at the same time. The catalyst contains $TeO_2$ in the range from 5 to 20, especially 7 to 12 wt. %, based on the total weight of the catalyst.

In order to achieve a better distribution of the active component and the promoter on the surface of the carrier, at least one chelating reagent is preferably present in the impregnation process. Said chelating reagents are chosen from carboxylic acids such as citric acid, tri-ammonium citrate, L-glutamic acid, tartaric acid and complexing agents such as ethylenediaminetetraacetic acid (EDTA), while the amount of chosen chelating agent added is 0.1-0.6 times by weight as much as that of the carrier and more preferably is 0.3-0.6 by weight. Ammonia should be added to adjust the pH value of the impregnating liquor to 8-10, the preferred operating procedure is an at least two step impregnation method comprising:

(1) when $K_2MoO_4$ is chosen as the precursor of the active compound, a given quantity of $H_6TeO_6$ according to the desired weight ratio is dissolved in a given quantity of distilled water to produce an aqueous solution, with which an according quantity of carrier is impregnated for 8-10 h, then dried at 100-135° C. for 4-6 h to produce an intermediate product; a given quantity of at least one chelating reagent and $K_2MoO_4$ are then dissolved in a given quantity of distilled water to produce an aqueous solution, into which a suitable amount of ammonia water is added to adjust the pH value to 8-10. The intermediate product produced above is impregnated with said solution for 8-10 h, finally said impregnated material is dried at elevated temperatures, especially at 110-135° C. for 4-6 h.

(2) When $(NH_4)_6Mo_7O_{24}\cdot 4H_2O$ plus one of the above-mentioned potassium compounds are chosen as the precursors of the active compound, the order of preparation is preferably as follows: first) a quantity of chosen potassium compound and a given quantity of $H_6TeO_6$ according to the desired weight ratio of Mo and Te are dissolved in a given quantity of distilled water to generate an aqueous solution. An according quantity of carrier is impregnated with said solution for 8-10 h, then dried at elevated temperatures, especially at 100-130° C. for 4-6 h to form a $H_6TeO_6$—K/$SiO_2$ intermediate product; a quantity of a chosen chelating reagent and $(NH_4)_6Mo_7O_{24}\cdot 4H_2O$ are then dissolved in a prescribed amount of distilled water to produce an aqueous solution, the pH value of which is adjusted to 8-10, by adding a suitable amount of ammonia water. Said intermediate product is then impregnated with said solution for 8-10 h, followed by drying it at elevated temperatures, especially at 110-135° C. for 4-6 h.

It is also possible to change the step sequence:

(3) A given quantity of $(NH_4)_6Mo_7O_{24}\cdot 4H_2O$ and a given quantity of $H_6TeO_6$ are dissolved in a given quantity of distilled water to generate an aqueous solution. A given quantity of $SiO_2$ is impregnated for 8-10 h, with said solution then dried at elevated temperatures, especially at 100-130° C. for 4-6 h to form a Mo—O—Te/$SiO_2$ intermediate product; a given quantity of potassium compound is dissolved in a given quantity of distilled water to produce an aqueous solution, into which a given quantity of the chosen chelating agent and ammonia water are added to adjust the pH value of the solution to 8-10, with which the Mo—O—Te/$SiO_2$ produced above is impregnated for 8-10 h, followed by drying at 110-135° C. for 4-6 h.

A continuous process for the manufacture of methyl mercaptan is successfully carried out by reacting a mixture of carbon oxides, sulphur or hydrogen sulphide and hydrogen at elevated temperatures and pressures in the presence of the above described catalysts.

The feed gas has preferable a hydrogen sulphide content in the range of 50-80 Vol. %.

It is preferred to feed the reactants carbon oxide, sulphur, hydrogen sulphide and hydrogen to the reactor in a molar ratio from 1/0/1/0 to 1/10/10/10, preferably from 1/0/2/2 to 1/0/10/10.

The reaction conditions as well as purification of the product and the recycling of non reacted compounds are generally known (U.S. Pat. No. 4,665,245/EP-A-104507; WO 2005/040082).

The catalyst should be pretreated with $H_2$ or syngas(CO+$H_2$) for 8-10 h preferably followed by sulfiding with $H_2S$ prior to the catalytic conversion of carbon monoxide, hydrogen and hydrogen sulphide to methanethiol to obtain the $TeO_2$ component of the promoter.

The evaluation of the catalytic performance of the catalyst in the present invention was carried out in a fixed-bed tubular reactor with 0.5 ml of catalyst per pass. The experiments were performed under the reaction conditions of CO/$H_2$/$H_2$S=1/1/2, 300° C., 0.2 MPa and GHSV=2000 $h^{-1}$. The products were analyzed by GC. All data were obtained after steady state conditions were achieved.

The following examples illustrate the present invention.

Example 1

Under stirring 0.648 g of $H_6TeO_6$ were fully dissolved in 10.0 ml of distilled water, the pH value of the aqueous solution of $H_6TeO_6$ thus prepared was measured to be 4.1, then 5.000 g of $SiO_2$ were impregnated with the aqueous solution of $H_6TeO_6$ at room temperature for 8 h, followed by drying at 120° C. for 5 h to produce a dried intermediate product.

Under stirring 2.068 g of $K_2MoO_4$ were fully dissolved in 5.0 ml of distilled water to produce a $K_2MoO_4$ aqueous solution, into which 5 ml of $NH_3\cdot H_2O$ were added, the pH value of the aqueous solution was measured to be 11.40, then, under stirring 3.000 g of citric acid were added to the aqueous solution of $K_2MoO_4$ plus $NH_3\cdot H_2O$, the pH value of the $K_2MoO_4$ plus $NH_3\cdot H_2O$ solution was measured to be 9.26. Finally, the intermediate product prepared in step (1) was impregnated with the solution containing citric acid $K_2MoO_4$ plus $NH_3\cdot H_2O$ at room temperature for 10 h, followed by drying at 120° C. for 5 h to generate a catalyst comprising $TeO_2$/$K_2MoO_4$/$SiO_2$, showing the weight ratio of 9/25/100. The evaluation results of the catalyst thus prepared are shown in table 1.

Example 2

(1) Under fast stirring, 1.468 g of $K_2CO_3$ and 0.648 g of $H_6TeO_6$ were fully dissolved in 10 ml of distilled water to form an aqueous solution, with which 5.000 g of $SiO_2$ were impregnated at room temperature for 9 h, and finally dried at 125° C. for 4 h to generate an intermediate product.

(2) 1.534 g of $(NH_4)_6Mo_7O_{24}\cdot 4H_2O$ were fully dissolved in 5.0 ml of distilled water under agitating to form an aqueous solution, to which 2.000 g of tri-ammonium citrate were added. Subsequently, a suitable amount of $NH_3\cdot H_2O$ was added to adjust the pH of the solution to 9.05. The intermediate product prepared in step (1) was impregnated with said solution at room temperature for 9 h and finally dried at 125° C. for 4 h to produce the catalyst $K_2O$/$MoO_3$/$TeO_2$/$SiO_2$, showing the weight ratio of 20/25/9/100. The evaluation results of the catalyst thus prepared are shown in table 1.

Example 3

The catalyst was prepared according to the method described in Example 1, but 2.000 g of tartaric acid was used as chelating reagent and the carrier $SiO_2$ was replaced by $\gamma$-$Al_2O_3$. The evaluation results of the catalyst thus prepared are shown in table 1.

Example 4 and 5

The catalyst was prepared according to the method described in Example 1, but the quantity of $H_6TeO_6$ was changed to be 0.486 g and 0.432 g respectively, and the chelating reagents used was EDTA in both cases, the weight ratio of the final catalysts thus prepared were $TeO_2$/$K_2MoO_4$/$SiO_2$=6.75/25/100 and $TeO_2$/$K_2MoO_4$/$SiO_2$=6/25/100 respectively. The evaluation results of the catalysts thus prepared are shown in table 1.

Example 6

The catalyst was prepared according to the method described in Example 1, but 5.000 g of $TiO_2$ was used as the carrier. The amount of $H_6TeO_6$ and the amount of $K_2MoO_4$ were replaced by 0.142 and 0.827 g, respectively. The final catalyst prepared was $TeO_2$/$K_2MoO_4$/$TiO_2$=2/10/100. The evaluation results of the catalyst thus prepared are shown in table 1.

Example 7

The catalyst was prepared according to the method described in Example 6, but 5.000 g of $ZrO_2$ was used as the carrier. and the amount of $H_6TeO_6$ and $K_2MoO_4$ was replaced by 0.071 g and 0.414 g respectively. The final catalyst prepared was $TeO_2/K_2MoO_4/ZrO_2=1/5/100$. The evaluation results of the catalyst thus prepared are shown in table 1.

Example 8

The catalyst was prepared according to the method described in Example 2, but 5.000 g of the mesoporous molecular sieve MCM-41 was used as the carrier, and the amount of $K_2CO_3$, $H_6TeO_6$ and $(NH_4)_6Mo_7O_{24}\cdot 4H_2O$ was replaced by 1.835 g, 1.080 g and 2.454 g, respectively. The final catalyst prepared was $K_2O/MoO_3/TeO_2/MCM-41=25/40/15/100$.

The evaluation results of the catalysts modified with different amounts of $TeO_2$ for methanethiol synthesis from high $H_2S$ containing feed gas are listed in table 1.

As it can be seen the addition of $TeO_2$ to $K_2MoO_4/SiO_2$ catalyst increases evidently the activity of the catalysts, which can find expression in the significant change of conversion of CO and the yield of $CH_3SH$. The conversion of CO reaches a maximum with 61.5% and a yield of methanethiol of 0.39 $g.ml_{cat}^{-1}.h^{-1}$. Obviously, both the conversion of CO and the yield of methanethiol do not correspond linearly or regularly as function of the amount of $TeO_2$ added.

TABLE 1

The evaluation results of the catalysts in examples 1-8.

| Example (catalyst) | Selectivity (%) | | | | $CO_2$/ $CH_3SH$ | Yield ($g\cdot ml_{cat}^{-1}\cdot h^{-1}$) | | | | Conv. of CO (%) |
|---|---|---|---|---|---|---|---|---|---|---|
| | $CH_4$ | $CH_3SH$ | COS | $CO_2$ | | $CH_4$ | $CH_3SH$ | COS | $CO_2$ | |
| 1, $K_2MoO_4/TeO_2/SiO_2 = 25/9/100$ | 0.23 | 55.21 | 10.70 | 33.86 | 0.61 | 0.0005 | 0.38 | 0.09 | 0.21 | 59.29 |
| 2, $K_2O/MoO_3/TeO_2/SiO_2 = 15/25/9/100$ | 0.25 | 55.15 | 11.30 | 33.30 | 0.60 | 0.0005 | 0.35 | 0.09 | 0.19 | 57.26 |
| 3, $K_2MoO_4/TeO_2/\gamma\text{-}Al_2O_3 = 25/9/100$ | 0.30 | 48.70 | 17.91 | 33.08 | 0.68 | 0.0005 | 0.24 | 0.09 | 0.21 | 56.02 |
| 4, $K_2MoO_4/TeO_2/SiO_2 = 25/6.75/100$ | 0.24 | 54.74 | 10.72 | 34.90 | 0.60 | 0.0005 | 0.35 | 0.09 | 0.21 | 56.02 |
| 5, $K_2MoO_4/TeO_2/SiO_2 = 25/6/100$ | 0.24 | 54.50 | 10.50 | 35.02 | 0.66 | 0.0005 | 0.36 | 0.09 | 0.22 | 57.52 |
| 6, $K_2MoO_4/TeO_2/TiO_2 = 10/2/100$ | 0.08 | 48.40 | 14.05 | 37.47 | 0.77 | 0.0005 | 0.31 | 0.09 | 0.24 | 48.4 |
| 7, $K_2MoO_4/TeO_2/ZrO_2 = 5/1/100$ | 0.09 | 48.17 | 17.84 | 33.90 | 0.70 | 0.0005 | 0.27 | 0.10 | 0.19 | 39.6 |
| 8, $K_2O/MoO_3/TeO_2/MCM-41 = 25/40/15/100$ | 0.07 | 51.28 | 11.83 | 36.82 | 0.72 | 0.0005 | 0.39 | 0.09 | 0.28 | 61.5 |

Example 9

FIG. 1 shows X-ray diffractograms of the catalyst $TeO_2$—$K_2MoO_4/SiO_2$ prepared by drying of the catalyst at 150° C. and calcination at 400° C. as compared to the starting materials and the catalysts $K_2MoO_4/SiO_2$ and CoO—$K_2MoO_4/SiO_2$ [A) carrier $SiO_2$; B) $H_6TeO_6$; C) $K_2MoO_4/SiO_2$; D) $TeO_2$—$K_2MoO_4/SiO_2$ (prepared with citric acid; drying at 150° C.); E) $TeO_2$—$K_2MoO_4/SiO_2$ (prepared with $HNO_3$ and without chelating reagent); F) CoO—$K_2MoO_4/SiO_2$; G) $TeO_2$—$K_2MoO_4/SiO_2$ (calcined at 400° C.); H) CoO—$K_2MoO_4/SiO_2$ (calcined at 500° C.)]. The diffractograms clearly demonstrate the distinct nature of the Te-containing catalysts as compared to other catalysts prepared on the basis of the system $K_2MoO_4/SiO_2$

The invention claimed is:

1. A supported catalyst for the preparation of methanethiol comprising
   a) a Mo and a K compound as active components, whereby Mo and K can be constituents of the same compound,
   b) a promoter, wherein the promoter comprises $TeO_2$ and
   c) an oxidic carrier
   wherein the weight ratios of the components are
   $TeO_2/K_2MoO_4/carrier=(1-20)/(1-50)/100$ or
   $TeO_2/MoO_3/K_2O/carrier=(1-20)/(1-50)/(1-50)/100$.

2. The catalyst according to claim 1, wherein the weight ratios of the components are
   (1) $TeO_2/K_2MoO_4/carrier=(3-12)/(15-30)/100$ or
   (2) $TeO_2/MoO_3/K_2O/carrier=(3-12)/(15-30)/(8-20)/100$.

3. The catalyst according to claim 1, wherein the carrier is selected from the group consisting of $SiO_2$, $Al_2O_3$, $TiO_2$, $Al_2O_3$—$SiO_2$, $ZrO_2$, zeolites, pure or mixtures of said metal oxides.

4. The catalyst according to claim 1, wherein the catalyst contains an active Mo—O—K center.

5. The catalyst according to claim 1, wherein the catalyst is sulfided by exposing to an hydrogen sulphide containing atmosphere.

6. The catalyst according to claim 1, wherein the $TeO_2$ content is in the range from 1 to 20 wt % of the catalyst.

* * * * *